(12) United States Patent (10) Patent No.: US 8,153,826 B2
Aoki et al. (45) Date of Patent: Apr. 10, 2012

(54) PROCESS FOR PRODUCTION OF (±)-3A,6,6,9A-TETRAMETHYLDECAHYDRO-NAPHTHO[2,1-B]FURAN-2(1H)-ONE

(75) Inventors: Takashi Aoki, Wakayama (JP); Yoshiharu Ataka, Wakayama (JP)

(73) Assignee: Kao Corporation, Tokyo (JP)

( * ) Notice: Subject to any disclaimer, the term of this patent is extended or adjusted under 35 U.S.C. 154(b) by 493 days.

(21) Appl. No.: 12/375,680

(22) PCT Filed: Jul. 27, 2007

(86) PCT No.: PCT/JP2007/064778
§ 371 (c)(1),
(2), (4) Date: Jan. 30, 2009

(87) PCT Pub. No.: WO2008/015977
PCT Pub. Date: Feb. 7, 2008

(65) Prior Publication Data
US 2009/0270639 A1 Oct. 29, 2009

(30) Foreign Application Priority Data
Jul. 31, 2006 (JP) .................. 2006-208487

(51) Int. Cl.
C07D 307/00 (2006.01)
(52) U.S. Cl. .................................. 549/299
(58) Field of Classification Search ............ 549/299
See application file for complete search history.

(56) References Cited

U.S. PATENT DOCUMENTS

| 4,503,240 A | 3/1985 | Staiger et al. |
| 5,290,955 A | 3/1994 | Asanuma et al. |

FOREIGN PATENT DOCUMENTS

| JP | 59 82381 | 5/1984 |
| JP | 04 099740 | 3/1992 |
| JP | 5 186452 | 7/1993 |
| JP | 05 202379 | 8/1993 |

OTHER PUBLICATIONS

Barrero, Alejandro F. et al., "Synthesis of (±)-Ambrox from (E)-Nerolidol and Beta-Ionone via Allylic Alcohol [2,3] Sigmatropic Rearrangement", J. Org. Chem., vol. 61, No. 6, pp. 2215-2218, (1996).
Hullot, Pierre et al., "Milieux hyperbasiques: preparation de carbanions en alph d'amides N,N-disubstitues. Synthese de Beta-et y-hydroxyamides et de y-butyrolactones", Can. J. of Chem., vol. 55, No. 2, pp. 266-273, (1977).
Sucrow, Wolfgang et al., "γ-Butyrolactone aus 4-Hydroxycarbonsaeure-dimethylamiden", Chem. Ber., vol. 108, No. 1, pp. 48-53, (1975).
Yoda, Hidemi et al., "First total synthesis of a new sesquiterpenoid natural product, (±)-3-(2,4-dihydroxybenzoyl)-4,5-dimethyl-5-(4,8-dimethyl-3(E),7(E)-nonadien-1-yl)tetrahydro-2-furanone", Tetrahedron Letters, Pergamon, vol. 44, pp. 1775-1777, (2003).
Günther Ohloff, et al., "212. Significance of the Geminal Dimethyl Group in the Odor Principle of Ambrox®'", Helvetica Chimica Acta, vol. 68, XP-002477422, Jan. 1, 1985, pp. 2022-2029.
Office Action issued Oct. 19, 2010, in Chinese Patent Application No. 200780027641.4 (English translation only).

*Primary Examiner* — Taylor Victor Oh
(74) *Attorney, Agent, or Firm* — Oblon, Spivak, McClelland, Maier & Neustadt, L.L.P.

(57) ABSTRACT

The present invention relates to industrially useful production processes in which (±)-3a,6,6,9a-tetramethyldecahydronaphtho[2,1-b]furan-2(1H)-ones and further (±)-3a,6,6,9a-tetramethyldo decahydronaphtho[2,1-b]furans are produced from raw materials which are readily available at low costs, through short steps and in a simple manner. The process for producing (±)-3a,6,6,9a-tetramethyldecahydronaphtho[2,1-b]furan-2(1H)-ones represented by the general formula (III):

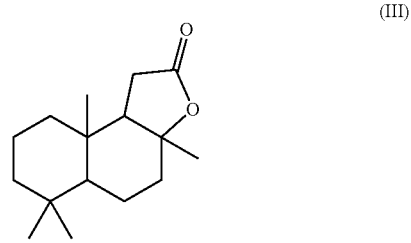

which includes the steps of cyclizing a homofarnesylic acid amide represented by the general formula (I):

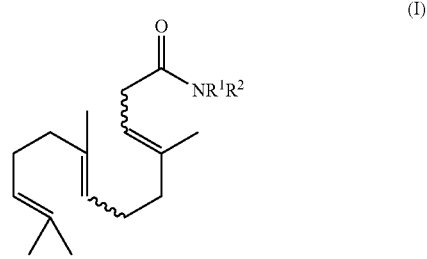

wherein $R^1$ and $R^2$ are each independently an alkyl group having 1 to 4 carbon atoms; and wavy lines each represents a carbon-to-carbon single bond having a cis or trans structure, and/or a monocyclohomofarnesylic acid amide represented by the general formula (II):

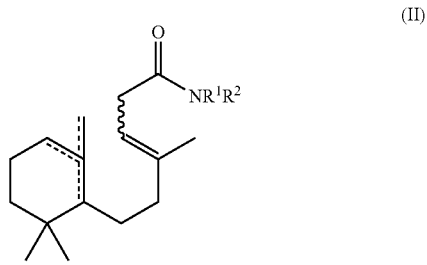

wherein $R^1$ and $R^2$ and wavy lines are the same as defined above; and dotted lines represent that a carbon-to-carbon double bond is present at any of positions represented by the dotted lines,
in the presence of an acid agent; and subjecting the cyclized product to hydrolysis.

19 Claims, No Drawings

PROCESS FOR PRODUCTION OF (±)-3A,6,6,9A-TETRAMETHYLDECAHYDRO-NAPHTHO[2,1-B]FURAN-2(1H)-ONE

CROSS REFERENCES TO RELATED APPLICATIONS

This application is a 371 of International Patent Application No. PCT/JP2007/064778, filed on Jul. 27, 2007, and claims priority to Japanese Patent Application No. 2006-208487, filed on Jul. 31, 2006.

FIELD OF THE INVENTION

The present invention relates to a novel process for producing (±)-3a,6,6,9a-tetramethyldecahydronaphtho[2,1-b]furan-2(1H)-ones.

BACKGROUND OF THE INVENTION

It is known that (±)-3a,6,6,9a-tetramethyl-(3aα,5aβ,9aα,9bβ)-decahydronaphtho[2,1-b]furan-2(1H)-one represented by the below-mentioned general formula (VI) (hereinafter occasionally referred to merely as "(±)-sclareolide") is one of diastereomers of (±)-3a,6,6,9a-tetramethyldecahydronaphtho[2,1-b]furan-2(1H)-ones represented by the below-mentioned general formula (III), and is a useful compound as a precursor, etc., for (±)-3a,6,6,9a-tetramethyl-(3aα, 5aβ,9aα, 9bβ)-dodecahydronaphtho[2,1-b]furan represented by the below-mentioned general formula (VII) (hereinafter occasionally referred to merely as "(±)-ambroxan") which is an important amber-like perfume material having, in particular, an excellent aromatizing property and an excellent fragrance persisting or lingering property among (±)-3a,6,6,9a-tetramethyldodecahydronaphtho[2,1-b]furans represented by the below-mentioned general formula (V).

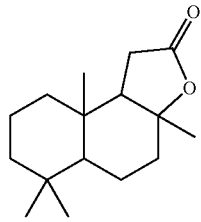

(III)

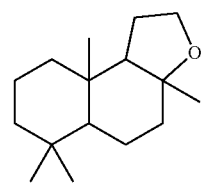

(V)

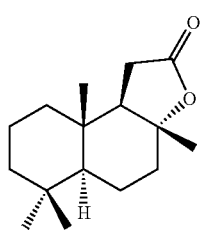

(VI)

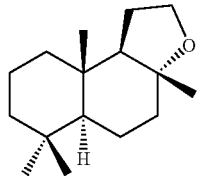

(VII)

The ambroxan inherently means (−)-ambroxan which is an optically active substance derived from natural substances. There are disclosed many processes for producing the ambroxan from (−)-sclareol as a starting material which is an extract from clary sage as a natural plant, via (+)-sclareolide (for example, refer to Non-Patent Document 1), and these processes have been practically used in industrial applications. However, these conventional production processes have problems such as less amounts of the natural raw materials supplied and unstable supply thereof. In addition, in the processes, since an oxidant such as chromic acid and permanganates is used in an oxidative decomposition step thereof, there also tends to occur such a problem that the processes have a large burden on environments.

For this reason, it has been demanded to develop an inexpensive process for producing the (±)-sclareolide and (±)-ambroxan from alternative petrochemical raw materials.

To meet the above demand, there is disclosed a process for producing (±)-ambroxan via (±)-sclareolide which includes, for example, six steps as shown in the following reaction formula (A) using farnesol or nerolidol as a starting material (for example, refer to Patent Document 1).

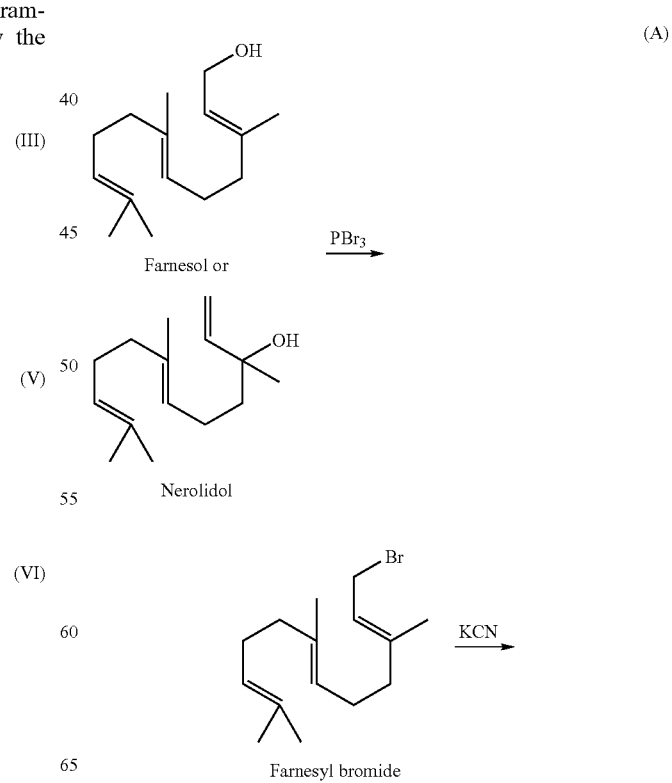

(A)

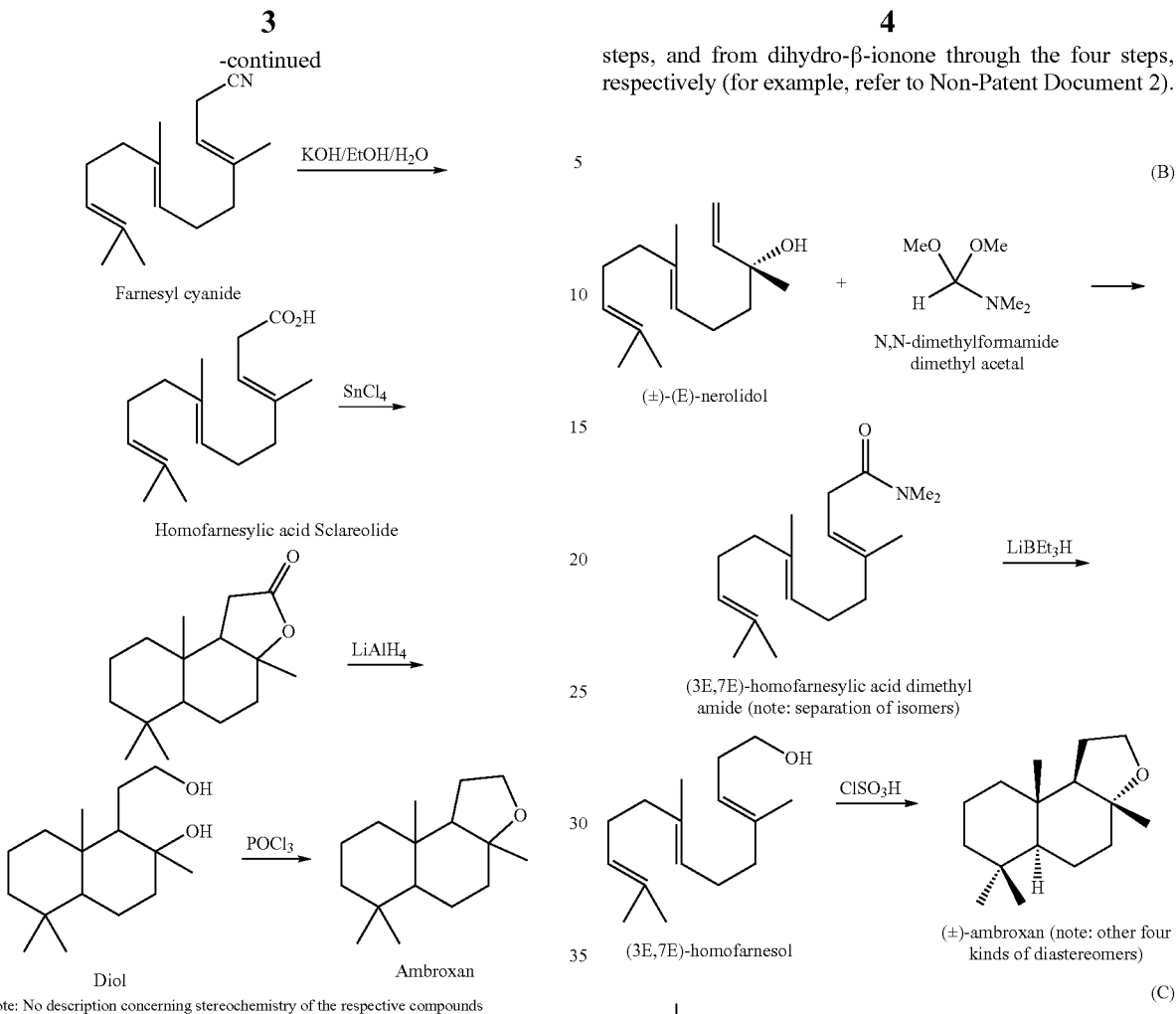

According to the above process, although the inexpensive raw material is converted into homofarnesylic acid with a relatively high yield, there tends to occur such a problem that the process is not fully suitable for industrial-scale production of the aimed compounds because the reagents having an extremely strong toxicity or corrosiveness such as potassium cyanide and phosphorus tribromide are used in an equimolar amount or more based on the raw material.

Further, there are many other reports describing a process for producing the compounds represented by the above general formula (III) by cyclizing homofarnesylic acid. From these reports, it is known that the diastereo-selectivity to the (±)-sclareolide largely varies depending upon kind of an acid agent and reaction conditions such as reaction temperature as used in the reaction. However, in order to produce, as a main reaction product, the (±)-sclareolide which is a more suitable diastereomer, it is advantageous to conduct the reaction in the presence of a very strong acid agent or under an extremely low temperature. Therefore, the above process is not fully suitable for industrial-scale production of the aimed compounds.

In addition, there are also many reports concerning the process for producing the (±)-ambroxan without via the (±)-sclareolide. In particular, there are known the processes represented by the following two reaction formulae (B) and (C) in which the compounds represented by the general formula (V) are obtained from (+)-(E)-nerolidol through the three steps, and from dihydro-β-ionone through the four steps, respectively (for example, refer to Non-Patent Document 2).

-continued

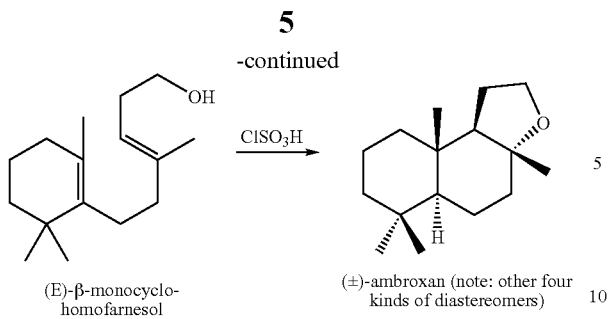

(E)-β-monocyclo-homofarnesol (±)-ambroxan (note: other four kinds of diastereomers)

These processes have such an advantage that the number of steps thereof is short as compared to those of the conventional processes for production of (±)-ambroxan. On the other hand, in these processes, a strong reducing agent (such as lithium triethyl boron hydride) having a risk of ignition due to violent reaction with water such as moisture in air must be used in the step of reducing the (3E,7E)-homofarnesylic acid dimethyl amide or (E)-β-monocyclo-homofarnesylic acid dimethyl amide into the respective corresponding alcohol compounds. As a result, these processes are not fully suitable for industrial-scale production of the aimed compounds.

Patent Document 1: DE 3240054

Non-Patent Document 1: "Tetrahedron", Vol. 43, p. 1871, 1987

Non-Patent Document 2: "Journal of Organic Chemistry", Vol. 61, p. 2215, 1996

SUMMARY OF THE INVENTION

The present invention relates to industrially useful production processes in which (±)-3a,6,6,9a-tetramethyldecahydronaphtho[2,1-b]furan-2(1H)-ones and further (±)-3a,6,6,9a-tetramethyldodecahydronaphtho[2,1-b]furans are produced from raw materials which are readily available at low costs, through short steps and in a simple manner.

The present inventors have found that the compounds represented by the general formula (III) are produced in an industrially advantageous manner by a novel reaction in which a homofarnesylic acid amide and/or a monocyclo-homofarnesylic acid amide readily obtained from inexpensive raw materials are directly subjected to cyclization reaction in the presence of an acid agent, and then the cyclized product is subjected to hydrolysis.

Thus, the present invention relates to a process for producing (±)-3a,6,6,9a-tetramethyldecahydronaphtho[2,1-b]furan-2(1H)-ones represented by the general formula (III):

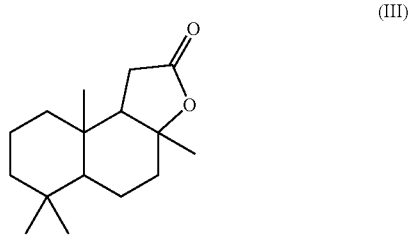

(III)

which includes the steps of cyclizing a homofarnesylic acid amide represented by the general formula (I):

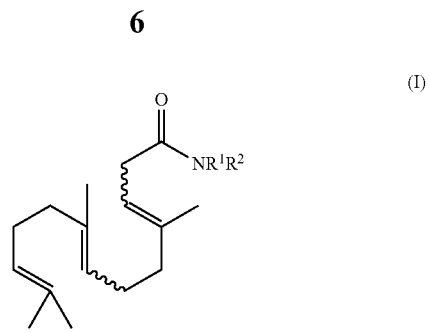

(I)

wherein $R^1$ and $R^2$ are each independently an alkyl group having 1 to 4 carbon atoms; and wavy lines each represents a carbon-to-carbon single bond having a cis or trans structure, and/or a monocyclohomofarnesylic acid amide represented by the general formula (II):

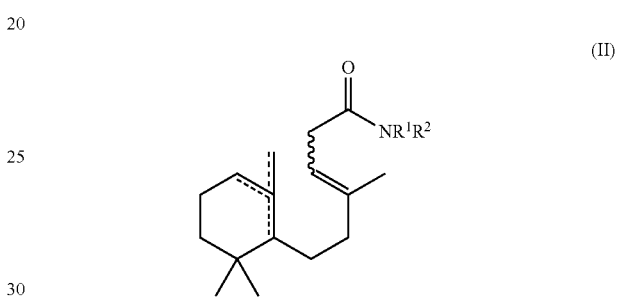

(II)

wherein $R^1$ and $R^2$ and wavy lines are the same as defined above; and dotted lines represent that a carbon-to-carbon double bond is present at any of positions represented by the dotted lines, in the presence of an acid agent; and subjecting the cyclized product to hydrolysis.

Effect of the Invention

According to the production processes of the present invention, the compounds represented by the general formula (III) and the compounds represented by the general formula (V) are produced in an industrially advantageous manner by a simple method with short steps in which a homofarnesylic acid amide and/or a monocyclohomofarnesylic acid amide readily obtained from inexpensive raw materials are directly subjected to cyclization reaction in the presence of an acid agent, and then the cyclized product is subjected to hydrolysis. In addition, according to the present invention, since it is not necessary to use a strong acid agent and an extremely low temperature which are generally required to enhance a yield and a diastereo-selectivity, the (±)-sclareolide represented by the general formula (VI) is obtained under more moderate conditions suitable for industrialization with a sufficiently high diastereo-selectivity.

DETAILED DESCRIPTION OF THE INVENTION

[Preparation of Homofarnesylic Acid Amide and Monocyclohomofarnesylic Acid Amide]

The homofarnesylic acid amide used in the present invention is a compound represented by the following general formula (I):

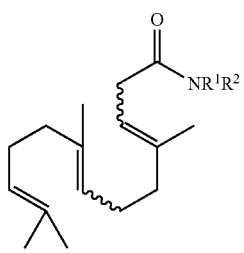 (I)

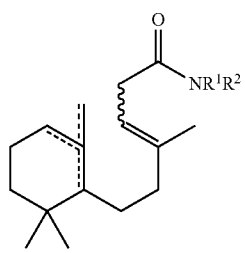 (II)

In the general formula (I), $R^1$ and $R^2$ are each independently an alkyl group having 1 to 4 carbon atoms; and wavy lines each represent a carbon-to-carbon single bond having a cis or trans structure. Examples of the alkyl group having 1 to 4 carbon atoms include methyl, ethyl, n-propyl, isopropyl, n-butyl, isobutyl and t-butyl. Among these alkyl groups, from the viewpoint of good availability, preferred is a methyl group.

The homofarnesylic acid amide may be produced, for example, by reacting (±)-nerolidol with N,N-dialkylformamide diacetal represented by the following general formula (VIII).

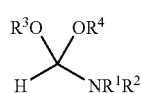 (VIII)

In the general formula (VIII), $R^1$ to $R^4$ are each independently an alkyl group having 1 to 4 carbon atoms. Examples of the alkyl group having 1 to 4 carbon atoms include methyl, ethyl, n-propyl, isopropyl, n-butyl, isobutyl and t-butyl. From the viewpoint of good availability, all of the $R^1$ to $R^4$ are most preferably methyl groups.

The (±)-nerolidol used as the raw material of the homofarnesylic acid amide may be those ordinarily available from the market. The (±)-nerolidol is in the form of a mixture of geometrical isomers including (E)-isomer and (Z)-isomer. Therefore, the homofarnesylic acid amide produced from the mixture of these geometrical isomers is also in the form of a mixture of four kinds of geometrical isomers including (3E, 7E)-isomer, (3Z,7E)-isomer, (3E, 7Z)-isomer and (3Z,7Z)-isomer. Similarly, the dihydro-ionone as the raw material of the monocyclohomofarnesylic acid amide has three kinds of geometrical isomers including α-isomer, β-isomer and γ-isomer which are different in position of double bond therein from each other. Therefore, when using a mixture of these geometrical isomers as the raw material, total six kinds of isomers of the monocyclohomofarnesylic acid amide are obtained. In the present invention, the respective ratios between the geometrical isomers in the (±)-nerolidol and the dihydro-ionone are not particularly limited. Therefore, the mixture of these geometrical isomers may be used as such as the raw material, or the (±)-nerolidol previously isolated into the respective isomers or the dihydro-ionone produced in a stereo-selective manner may also be used. The resulting homofarnesylic acid amide or monocyclohomofarnesylic acid amide in the form of a mixture of these geometrical isomers may be subjected as such to cyclization reaction, or may be previously isolated into the respective isomers before being subjected to the cyclization reaction.

The monocyclohomofarnesylic acid amide used in the present invention is a compound represented by the following general formula (II):

In the general formula (II), $R^1$ and $R^2$ and wavy lines are the same as defined above; and dotted lines represent that a carbon-to-carbon double bond is present at any of positions represented by the dotted lines.

The monocyclohomofarnesylic acid amide may be produced by reacting the dihydro-ionone, for example, with vinyl magnesium bromide, or by adding acetylene to the dihydro-ionone and then subjecting the resulting addition product to selective hydrogenation in the presence of a Lindlar catalyst, etc., to obtain (±)-monocyclonerolidol, followed by reacting the thus obtained (±)-monocyclonerolidol with N,N-dialkylformamide diacetal similarly to the above production of the homofarnesylic acid amide.

[Preparation of Compounds Represented by the General Formula (III)]

In the process for producing the compounds represented by the general formula (III) according to the present invention, the homofarnesylic acid amide represented by the general formula (I) and/or the monocyclohomofarnesylic acid amide represented by the general formula (II) are first added dropwise to a mixed solution of an acid agent and a solvent to subject these compounds to cyclization reaction, thereby obtaining a cyclic enamine derivative as shown in the below-mentioned reaction formula (D).

Examples of the acid agent used in the cyclization reaction include sulfuric acid, Brønstead acids having an acidity identical to or higher than that of sulfuric acid, such as or methanesulfonic acid, p-toluenesulfonic acid, chlorosulfonic acid and trifluoromethanesulfonic acid, and Lewis acids such as metal chlorides and boron trifluoride ether complexes. From the viewpoint of a good diastereo-selectivity to the (±)-sclareolide, any of these acid agents may be used. Therefore, among these acid agents, sulfuric acid, methanesulfonic acid, chlorosulfonic acid, tin tetrachloride and titanium tetrachloride are preferably used from the viewpoints of low costs and easiness of handling.

The acid agent may be used in an amount of from 0.1 to 10 moles per 1 mole of the homofarnesylic acid amide and/or the monocyclohomofarnesylic acid amide as the raw materials. In order to completely convert the raw materials into the aimed products, the acid agent is preferably used in an amount of 2 moles or more per 1 mole of the raw materials. Further, from the viewpoints of low production costs and a less burden upon post treatments, the acid agent is preferably used in an amount of 7 moles or less per 1 mole of the raw materials.

The cyclization reaction may be carried out under a solvent-free condition. However, from the viewpoint of preventing reduction in yield owing to polymerization of the raw materials, the cyclization reaction is preferably carried out in a solvent which is present in an amount of from 1 to 100 parts by mass per one part by mass of the homofarnesylic acid amide and/or the monocyclohomofarnesylic acid amide as the raw materials. The solvent used in the cyclization reaction is not particularly limited as long as they are selected from hydrocarbons, halogenated hydrocarbons, nitro-hydrocarbons and ethers which are inert to the reaction in the presence of the acid agent. From the viewpoint of facilitated recovery procedure, among these solvents, preferred are non-water-soluble solvents, and further from the viewpoint of low costs, more preferred are dichloromethane, chloroform, toluene and xylene.

The homofarnesylic acid amide and/or the monocyclo-homofarnesylic acid amide as the raw materials may be dissolved in these solvents, or may be added dropwise to the acid agent while stirring under the solvent-free condition. From the viewpoint of a good productivity, the raw materials are preferably added dropwise to the acid agent under the solvent-free condition. The dropping velocity of the raw materials may be optionally determined unless the dropping causes rapid increase in temperature of the reaction solution.

The cyclization reaction may be carried out in a temperature range of from −70 to 100° C. From the viewpoint of a less burden of facilities upon industrialization, the cyclization reaction temperature is preferably −20° C. or higher. In addition, from the viewpoint of suppressing occurrence of side reactions such as polymerization, the cyclization reaction temperature is preferably 50° C. or lower, and from the viewpoint of attaining a high selectivity to the (±)-sclareolide, the cyclization reaction temperature is more preferably 10° C. or lower.

Thus, in accordance with the present invention, since neither a strong acid agent nor an extremely low reaction temperature which are generally needed to obtain a high diastereo-selectivity are required, the compound represented by the following general formula (VI) ((±)-sclareolide) can be produced with a sufficiently high diastereo-selectivity thereto under more moderate condition suitable for industrialization.

(VI)

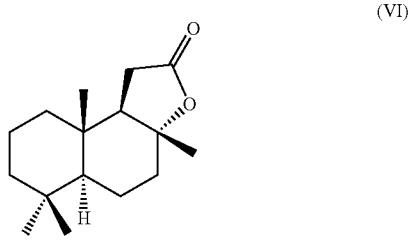

The mechanism of the reaction of the present invention is not fully made clear. However, as shown below in the reaction formula (D), it is suggested that the cyclic enamine derivative obtained after completion of dropping the raw material is hydrolyzed and thereby converted into the compound represented by the general formula (III).

(D)

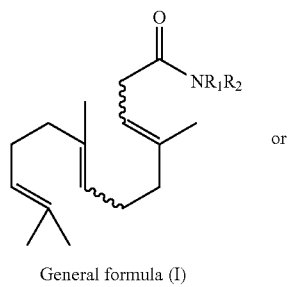

General formula (I)

-continued

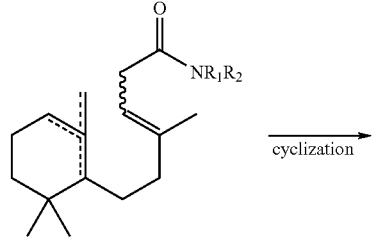

General formula (II)

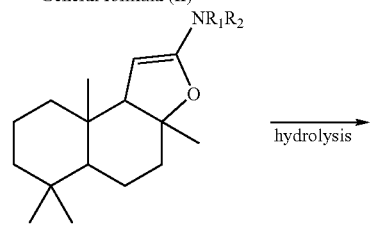

Cyclic enamine derivatibe

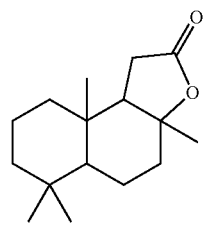

General formula (III)

After completion of dropping the raw material, water is added to the cyclic enamine derivative, and the resulting reaction mixture is stirred in a temperature range of from 0° C. to a boiling point of the solvent while keeping the acid condition until confirming dissipation of the cyclic enamine derivative as the intermediate product.

In this case, after completion of dropping the raw material, the acid agent may be once neutralized with a base agent to remove the resulting salt therefrom, and then the other acid agent may be newly added in an amount of from 0.01 to 5 moles per 1 mole of the homofarnesylic acid amide and/or the monocyclohomofarnesylic acid amide as the raw materials to conduct the hydrolysis. Examples of the other acid agent include carboxylic acids having a weak acidity such as acetic acid, dilute hydrochloric acid and dilute sulfuric acid.

After completion of the hydrolysis, the acid agent is neutralized, and then the resulting reaction solution is extracted with an organic solvent, and removal of the solvent from the resulting extract is conducted to obtain the compound represented by the general formula (III).

[Preparation of Compounds Represented by General Formula (V)]

The compound represented by the general formula (V) may be produced by subjecting the compound represented by the general formula (III) to reduction and cyclization by the known methods as described in the Patent Document 1, the Non-Patent Document 1 or the like. More specifically, as shown in the following reaction formula (E), the compound represented by the general formula (III) is subjected to reduction reaction in the co-existence of a reducing agent such as lithium aluminum hydride to obtain the (±)-diol represented by the general formula (IV), and then the thus obtained (±)-diol is cyclized in the co-existence of a dehydration agent such as phosphorus oxychloride to thereby obtain the compound represented by the general formula (V)

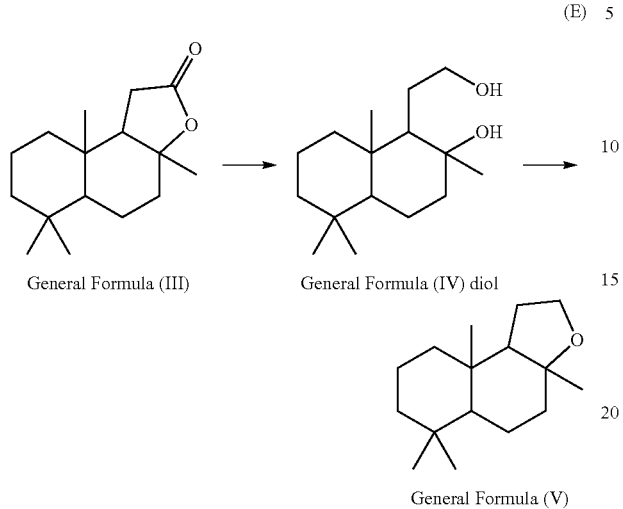

In addition, the resulting compound represented by the general formula (V) may also be subjected to recrystallization or column chromatography to separate the compound into the respective isomers, thereby enhancing a purity of the (±)-ambroxan as a preferred amber aroma ingredient.

EXAMPLES

The present invention will be described in more detail below by referring to the following Examples and Comparative Examples. However, the following Examples are only illustrative and not intended to limit the invention thereto.
(1) Determination of Yield The yield of the respective compounds obtained in Examples and Comparative Examples was determined by an internal standard quantitative analysis method using a gas chromatography. However, the quantitative analysis of diastereomers of the (±)-sclareolide and the (±)-ambroxan was carried out using a calibration curve for each of the (±)-sclareolide and the (±)-ambroxan.

Synthesis Example 1

Synthesis of Homofarnesylic Acid Dimethyl Amide

To 200 g of xylene were added 222 g of (±)-nerolidol (1.0 mol; geometrical isomer ratio E/Z:60/40) and 135 g of N,N-dimethylformamide dimethyl acetal (1.1 mol), and the resulting mixture was stirred under reflux for 24 h while distilling off methanol by-produced therefrom. After distilling off the solvent, the resulting reaction solution was subjected to distillation under reduced pressure to obtain 211 g of a mixture of four geometrical isomers of homofarnesylic acid dimethyl amide (purity: 97%; yield: 74%). As a result of analyzing the thus obtained mixture by liquid chromatography, it was confirmed that the ratios of the respective geometrical isomers were 32% for (3E,7E)-isomer, 27% for (3Z,7E)-isomer, 22% for (3E,7Z)-isomer and 19% for (3Z,7Z)-isomer.

Synthesis Example 2

Synthesis of (±)-β-Monocyclonerolidol

Into 300 mL of anhydrous tetrahydrofuran was dissolved 194 g of dihydro-β-ionone (1.0 mol). After cooling the obtained solution to 100° C., an anhydrous THF solution containing 104 g of magnesium vinyl bromide (1.2 mol) was added dropwise thereto, and the obtained mixture was further stirred at 10° C. for 1 h. Next, while cooling the mixture to 0° C., 400 mL of a 10% ammonium chloride aqueous solution was added dropwise thereto, and the obtained mixture was separated into a water layer and an organic layer. The thus separated water layer was extracted with diethyl ether twice. The thus obtained organic layers were mixed together, washed with a saturated sodium hydrogencarbonate aqueous solution and saturated brine, and then dried. After distilling off the solvent, the reaction solution was further subjected to distillation under reduced pressure, thereby obtaining 199 g of (±)-β-monoclonerolidol (purity: 94%; yield: 84%).

Synthesis Example 3

Synthesis β-Monocyclohomofarnesylic Acid Dimethyl Amide

To 100 g of xylene were added 47 g of (±)-β-monoclonerolidol (purity: 94%; 0.20 mol) produced in Synthesis Example 2 and 52 g of N,N-dimethylformamide dimethyl acetal (0.44 mol), and the resulting mixture was subjected to the same procedure as in Synthesis Example 1, thereby obtaining 51 g of a mixture of two geometrical isomers of β-monocyclohomofarnesylic acid dimethyl amide (purity: 90%; yield: 82%). As a result of analyzing the thus obtained mixture by liquid chromatography, it was confirmed that the ratios of the respective geometrical isomers were 58% for (E)-isomer and 42% for (Z)-isomer.

Example 1

Synthesis (1) of Compound Represented by General Formula (III)

A mixed solution containing 2.2 g of concentrated sulfuric acid (21 mmol) and 20 g of dichloromethane was cooled to 0° C., and a 10% dichloromethane solution containing 2.0 g of homofarnesylic acid dimethyl amide (purity: 97%; 7.0 mmol) produced in Synthesis Example 1 was added dropwise to the mixed solution over 2 h. The resulting mixture was mixed with 10 g of water and then stirred at 25° C. for 2 h. After neutralizing a water layer of the resulting reaction solution with a sodium hydroxide aqueous solution, an organic layer was separated from the reaction solution, and the water layer thus separated from the organic layer was extracted with 10 g of dichloromethane twice. The thus obtained organic layers were mixed together, washed with saturated brine and then dried, and further the solvent was distilled off therefrom, thereby obtaining 1.8 g of an orange solid. As a result of analyzing the thus obtained solid, it was confirmed that the orange solid contained the compounds represented by the general formula (III) in a total amount of 1.2 g (yield: 68%), and the diastereo-selectivity to the (±)-sclareolide was 41%.

Examples 2 to 5

Synthesis (2) of Compound Represented by General Formula (III)

The reaction was carried out in the same manner as in Example 1 except that the solvent and the temperature condition used therein were varied as shown in Table 1. The results of the yield and selectivity are enumerated in Table 1 in which the yield was the value of the compound represented by the general formula (III), whereas the selectivity was the value of the (±)-sclareolide.

TABLE 1

| Examples | Acid agent (mol per mol of amide) | Solvent | Temperature (°C.) | Yield (%) | Selectivity (%) |
|---|---|---|---|---|---|
| 2 | Sulfuric acid (3.0) | Toluene | 0 | 45 | 38 |
| 3 | Methanesulfonic acid (6.0) | Dichloromethane | 0 | 46 | 49 |
| 4 | Chlorosulfonic acid (6.0) | Dichloromethane | −60 | 45 | 30 |
| 5 | Tin tetrachloride (6.0) | Dichloromethane | −20 | 22 | 36 |

Example 6

Synthesis (3) of Compound Represented by General Formula (III)

A mixed solution containing 2.3 g of concentrated sulfuric acid (23 mmol) and 20 g of toluene was cooled to 0° C., and a 10% toluene solution containing 2.4 g of β-homofarnesylic acid dimethyl amide 1 (purity: 90%; 7.7 mmol) produced in Synthesis Example 3 was added dropwise to the mixed solution over 30 min. The resulting reaction solution was neutralized with a sodium hydroxide aqueous solution, and the water layer was once removed therefrom. Thereafter, 10 g of water was added again together with 1.0 g of acetic acid (17 mmol) to the solution, and the resulting mixture was stirred under reflux for 5 h. After cooling to room temperature, the obtained reaction solution was neutralized with a saturated sodium hydrogencarbonate aqueous solution, and the water layer separated from the solution was extracted with 10 g of toluene twice. The thus obtained organic layers were mixed together, washed with saturated brine and then dried, and further the solvent was distilled off therefrom, thereby obtaining 2.4 g of a dark red solid. As a result of analyzing the thus obtained solid, it was confirmed that the dark red solid contained the compounds represented by the general formula (III) in a total amount of 0.79 g (yield: 41%), and the diastereo-selectivity to the (±)-sclareolide was 50%.

Example 7

Synthesis (4) of Compound Represented by General Formula (III)

The reaction was carried out in the same manner as in Example 1 except that the reaction temperature was changed from 0° C. to 20° C. As a result of analyzing the obtained reaction product, it was confirmed that the yield of the compounds represented by the general formula (III) was 63%, and the diastereo-selectivity to the (±)-sclareolide was 30%.

Example 8

Synthesis (5) of Compound Represented by General Formula (III)

The reaction was carried out in the same manner as in Example 1 except that the reaction temperature was changed from 0° C. to 40° C. As a result of analyzing the obtained reaction product, it was confirmed that the yield of the compounds represented by the general formula (III) was 63%, and the diastereo-selectivity to the (±)-sclareolide was 25%.

Example 9

Synthesis of Compound Represented by General Formula (III)

A mixed solution containing 90 g of concentrated sulfuric acid (0.86 mol) and 100 g of dichloromethane was cooled to 0° C., and 86 g of homofarnesylic acid dimethyl amide (purity: 97%; 0.3 mol) produced in Synthesis Example 1 was added dropwise to the mixed solution over 3 h. The resulting reaction solution was neutralized with a sodium hydroxide aqueous solution, and the water layer was once removed therefrom. Thereafter, 100 g of tetrahydrofuran and 50 g of 20% sulfuric acid (0.10 mol) were added to the organic layer thus separated from the water layer, and the resulting mixture was stirred under reflux for 10 h. The obtained reaction solution was neutralized again with a sodium hydroxide aqueous solution, and the water layer separated from the solution was extracted with 30 g of dichloromethane twice. The thus obtained organic layers were mixed together, washed with saturated brine and then dried, and further the solvent was distilled off therefrom, thereby obtaining 79 g of a dark red solid. As a result of analyzing the thus obtained solid, it was confirmed that the dark red solid contained the compounds represented by the general formula (III) in a total amount of 56 g (yield: 75%), and the diastereo-selectivity to the (±)-sclareolide was 40%.

Example 10

Synthesis of Compound Represented by General Formula (IV)

Into 10 g of anhydrous diethyl ether was suspended 0.28 g (7.4 mmol) of lithium aluminum hydride, and the resulting suspension was cooled to 0° C. Then, a solution prepared by dissolving 2.0 g of a solid containing 0.91 g (3.7 mmol) of the compound represented by the general formula (III) which was produced in Example 1, in 10 g of anhydrous diethyl ether was added dropwise to the suspension over 15 min. After completion of the dropping, the resulting mixture was further stirred under reflux for 1 h. After cooling the obtained reaction solution to room temperature, 15 g of a 10% sodium hydroxide aqueous solution was added dropwise thereto, and the water layer separated from the solution was extracted with 10 g of diethyl ether twice. The thus obtained organic layers were mixed together, washed with a saturated ammonium chloride aqueous solution and then dried, and further the solvent was distilled off therefrom, thereby obtaining 2.1 g of a light yellow semi-solid. As a result of analyzing the thus obtained semi-solid, it was confirmed that the semi-solid contained the compounds represented by the general formula (IV) in a total amount of 0.89 g (yield: 96%).

Example 11

Synthesis of Compound Represented by General Formula (V)

A solution prepared by dissolving 1.7 g of the semi-solid containing 0.70 g (2.8 mmol) of the compound represented by the general formula (IV) which was produced in Example 9, in 20 g of anhydrous pyridine, was cooled to 0° C., and 0.52 g (3.4 mmol) of phosphorus oxychloride was added dropwise thereto over 5 min, and the resulting mixture was further stirred for 2 h. Successively, 10 g of a 10% sodium hydroxide aqueous solution was added dropwise to the resulting reaction solution at 0° C., and the water layer separated from the solution was extracted with 10 g of diethyl ether twice. The thus obtained organic layers were mixed together, washed with a saturated ammonium chloride aqueous solution and then dried, and further the solvent was distilled off therefrom, thereby obtaining 1.5 g of a yellow oily substance. As a result of analyzing the thus obtained oily substance, it was confirmed that the oily substance contained the compounds represented by the general formula (V) in a total amount of 0.44 g (yield: 68%), and the diastereo-purity of ambroxan was 44%.

Industrial Applicability

In accordance with the production process of the present invention, the compounds represented by the general formula (III) and the compounds represented by the general formula (V) can be produced with a sufficiently high diastereo-selectivity under more moderate conditions suitable for industrialization, thereby enabling these compounds to be produced in an industrially advantageous manner. In addition, according to the present invention, since the use of a strong acid agent and an extremely low reaction temperature which are generally needed for enhancing a diastereo-selectivity is not required, the (±)-sclareolide represented by the general formula (IV) can be produced with a sufficiently high diastereo-selectivity under more moderate conditions suitable for industrialization thereof.

The invention claimed is:

1. A process for producing a (±)-3a,6,6,9a-tetramethyl decahydronaphtho[2,1-b]furan-2(1H)-one represented by formula (III):

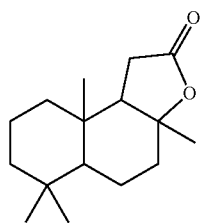

(III)

comprising:
cyclizing one or more compounds selected from the group consisting of:
(a) a homofarnesylic acid amide represented by formula (I):

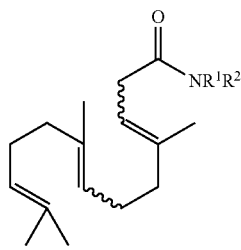

(I)

wherein $R^1$ and $R^2$ are each independently an alkyl group having 1 to 4 carbon atoms;

and each wavy line represents a carbon-to-carbon single bond having a cis or trans structure;

(b) a monocyclohomofarnesylic acid amide represented by formula (II):

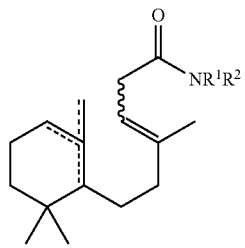

(II)

wherein $R^1$ and $R^2$ and each wavy line are the same as defined above; and the dotted lines indicate that a carbon-to-carbon double bond is present at any one of the positions having a dotted line; and (c) a mixture thereof, in the presence of an acid agent, to obtain a cyclized product; and subjecting said cyclized product to hydrolysis.

2. A process according to claim 1, comprising cyclizing a homofarnesylic acid amide represented by formula (I).

3. A process according to claim 1, comprising cyclizing a monocyclohomofarnesylic acid amide represented by formula (II).

4. A process according to claim 1, comprising cyclizing a mixture of a homofarnesylic acid amide represented by formula (I) and a monocyclohomofarnesylic acid amide represented by formula (II).

5. A process according to claim 1, wherein $R^1$ and $R^2$ are each a methyl group.

6. A process according to claim 2, wherein $R^1$ and $R^2$ are each a methyl group.

7. A process according to claim 3, wherein $R^1$ and $R^2$ are each a methyl group.

8. A process according to claim 1, wherein said acid agent is one or more acids selected from the group consisting of sulfuric acid, methanesulfonic acid, p-toluenesulfonic acid, chlorosulfonic acid, trifluoromethanesulfonic acid, a metal chloride, and a boron trifluoride ether complex.

9. A process according to claim 2, wherein said acid agent is one or more acids selected from the group consisting of sulfuric acid, methanesulfonic acid, p-toluenesulfonic acid, chlorosulfonic acid, trifluoromethanesulfonic acid, a metal chloride, and a boron trifluoride ether complex.

10. A process according to claim 3, wherein said acid agent is one or more acids selected from the group consisting of sulfuric acid, methanesulfonic acid, p-toluenesulfonic acid, chlorosulfonic acid, trifluoromethanesulfonic acid, a metal chloride, and a boron trifluoride ether complex.

11. A process according to claim 1, wherein said acid agent is one or more acids selected from the group consisting of sulfuric acid, methanesulfonic acid, chlorosulfonic acid, tin tetrachloride, and titanium tetrachloride.

12. A process according to claim 2, wherein said acid agent is one or more acids selected from the group consisting of sulfuric acid, methanesulfonic acid, chlorosulfonic acid, tin tetrachloride, and titanium tetrachloride.

13. A process according to claim 3, wherein said acid agent is one or more acids selected from the group consisting of sulfuric acid, methanesulfonic acid, chlorosulfonic acid, tin tetrachloride, and titanium tetrachloride.

14. A process according to claim 1, wherein said acid agent is a Brɸnstead acid having an acidity identical to or higher than that of sulfuric acid, or a Lewis acid.

15. A process according to claim 1, wherein said acid agent is used in an amount of from 0.1 to 10 moles per 1 mole of said homofarnesylic acid amide and/or said monocyclohomofarnesylic acid amide.

16. A process according to claim 1, wherein said cyclizing is carried out at a temperature of from −70 to 100° C.

17. A process according to claim 1, wherein said cyclizing is carried out in at least one solvent selected from the group consisting of a hydrocarbon, a halogenated hydrocarbon, a nitro-hydrocarbon, and an ether.

18. A process according to claim 1, wherein said cyclizing is carried out in at least one solvent selected from the group consisting of dichloromethane, chloroform, toluene, and xylene.

19. A process according to claim 1, wherein said cyclizing is carried out in a solvent which is present in an amount of from 1 to 100 parts by mass per one part by mass of said homofarnesylic acid amide and/or said monocyclohomofarnesylic acid amide.

* * * * *